United States Patent [19]

Gaffar et al.

[11] Patent Number: 5,037,637

[45] Date of Patent: * Aug. 6, 1991

[54] ANTIBACTERIAL ANTIPLAQUE, ANTICALCULUS ORAL COMPOSITION

[75] Inventors: Abaul Gaffar, Princeton; Nuran Nabi, North Brunswick; Brian S. Jannone, Basking Ridge, all of N.J.

[73] Assignee: Colgate-Palmolive Company, Piscataway, N.J.

[*] Notice: The portion of the term of this patent subsequent to Jan. 16, 2007 has been disclaimed.

[21] Appl. No.: 447,745

[22] Filed: Dec. 8, 1989

Related U.S. Application Data

[63] Continuation of Ser. No. 346,258, May 1, 1989, which is a continuation of Ser. No. 8,901, Jan. 30, 1987, abandoned.

[51] Int. Cl.$^5$ .................. A61K 7/22; A61K 7/16; A61K 7/18
[52] U.S. Cl. ........................ 424/52; 424/48; 424/49; 424/54; 424/56; 424/57; 514/835
[58] Field of Search .................. 424/49, 52, 54, 48, 424/56, 57; 514/835

[56] References Cited

U.S. PATENT DOCUMENTS

| | | | |
|---|---|---|---|
| 1,943,467 | 1/1934 | Bley | 424/50 |
| 4,627,977 | 12/1986 | Gaffar et al. | 424/52 |
| 4,980,153 | 12/1990 | Jackson et al. | 424/52 |

FOREIGN PATENT DOCUMENTS

| | | |
|---|---|---|
| 0161898 | 11/1985 | European Pat. Off. . |
| 0236290 | 9/1987 | European Pat. Off. . |
| 0251591 | 1/1988 | European Pat. Off. . |
| 0506292 | 4/1971 | Switzerland . |

*Primary Examiner*—Ronald W. Griffin
*Attorney, Agent, or Firm*—Robert L. Stone; Murray M. Grill

[57] ABSTRACT

An oral composition such as a dentifrice, mouthwash, lozenge or chewing gum containing a polyphosphate anticalculus agent, such as tetraalkali metal pyrophosphate and antibacterial antiplaque agent compatible therewith. The antiplaque agent is a substantially water-insoluble noncationic antibacterial agent such as 2,4,4'-tricholoro-2$^1$-hydroxydiphenyl ether (Triclosan).

26 Claims, No Drawings

ANTIBACTERIAL ANTIPLAQUE, ANTICALCULUS ORAL COMPOSITION

This is a continuation of application Ser. No. 346,258, filed May 1, 1989, which is a continuation of Ser. No. 008,901, filed Jan. 30, 1987, now abandoned.

This invention relates to an antibacterial antiplaque anticalculus oral composition. More particularly, it relates to an oral composition containing a polyphosphate anticalculus (that is, antitartar) agent and a compatible antibacterial agent effective to inhibit plaque.

In U.S. Pat. Nos. 4,627,977 to Gaffar et al; 4,515,772 to Parran et al; and 4,323,551 to Parran, oral compositions are described which include various polyphosphate compounds. In the patent to Gaffar et al, a linear molecular dehydrated polyphosphate salt is employed in conjunction with a fluoride ion-providing source and a synthetic linear polymeric polycarboxylate to inhibit calculus formation.

In the patents to Parran et al and to Parran water soluble dialkali metal pyrophosphate alone or mixed with tetraalkali metal pyrophosphate is employed.

Oral compositions which inhibit calculus formation on dental surfaces are highly desirable since calculus is one of the causitive factors in periodontal conditions. Thus, its reduction promotes oral hygiene.

Dental plaque is a precursor of calculus. Unlike calculus, however, plaque may form on any part of the tooth surface, particularly including at the gingival margin. Hence, besides being unsightly, it is implicated in the occurence of gingivitis.

Accordingly, it would be highly desirable to include antimicrobial agents which have been known to reduce plaque in oral compositions containing anticalculus agents. Indeed, this has been described in U.S. Pat. No. 4,022,550 to Vinson et al, wherein a compound providing zinc ions as an anticalculus agent is admixed with an antibacterial agent effective to retard the growth of plaque bacteria. wide variety of antibacterial agents are described with the zinc compounds including cationic materials such as guanides and quaternary ammonium compounds as well as non-cationic compounds such as halogenated salicylanilides and halogenated hydroxydiphenyl ethers.

Hitherto, the cationic antibacterial materials such as chlorhexidine, benzethonium chloride and cetyl pyridinium chloride have been the subject of greatest investigation as antibacterial antiplaque agents. However, in spite of their being used in conjuction with zinc anticalculus agent, they are not effective when used with anionic materials such as polyphosphate anticalculus agent. This ineffectiveness is considered to be quite surprising as polyphosphates are chelating agents and the chelating effect has previously been known to increase the efficacy of cationic antibacterial agents.(see e.g. *Disinfection, Sterilization and Preservation*, 2nd Ed., Black, 1977, page 915 and *Inhibition and Destruction of the Microbial Cell*, Hugo, 1971, page 215). Indeed, quaternary ammonium compound is present in the plaque control mouthwash containing pyrophosphate of U.S. Pat. No. 4,323,551 and bis-biguanide antiplaque agent is suggested in the anticalculus pyrophosphate oral composition of U.S. Pat. No. 4,515,772.

In view of the surprising incompatibility of cationic antibacterial agents with polyphosphates present as anticalculus agents, it was quite unexpected that other antibacterial agent would be effective.

It is an advantage of this invention that certain antibacterial agents are effective in anticalculus oral compositions to inhibit plaque formation.

It is a further advantage of this invention that a composition is provided which is effective to reduce plaque and calculus formation.

It is a further advantage of this invention that an antiplaque, anticalculus oral composition is provided which is effective to reduce the occurence of gingivitis.

Additional advantages of this invention will be apparent from consideration of the following specification.

In accordance with certain of its aspects this invention relates to an oral composition comprising in an orally acceptable vehicle, an effective anticalculus amount of material comprising at least one linear molecularly dehydrated polyphosphate salt as essential anticalculus agent and an effective antiplaque amount of a substantially water insoluble noncationic antibacterial agent selected from the group consisting of halogenated diphenyl ethers, phenolic compounds, benzoate esters, and halogenated carbanilides.

Typical examples of antibacterial agents which are particularly desirable from consideration of antiplaque effectiveness, safety and formulation are:

Halogenated Diphenyl Ethers
2',4,4'-trichloro-2-hydroxy-diphenyl ether (Triclosan)
2,2'-dihydroxy-5,5'-dibromo-diphenyl ether.
Phenolic Compounds
(including phenol and its homologs, mono-
and poly-alkyl and aromatic halophenols, resorcinol and its
derivatives and bisphenolic compounds and Phenol and its Homologs Phenol

| | |
|---|---|
| 2 Methyl | - Phenol |
| 3 Methyl | - Phenol |
| 4 Methyl | - Phenol |
| 4 Ethyl | - Phenol |
| 2,4-Dimethyl | - Phenol |
| 2,5-Dimethyl | - Phenol |
| 3,4-Dimethyl | - Phenol |
| 2,6-Dimethyl | - Phenol |
| 4-n-Propyl | - Phenol |
| 4-n-Butyl | - Phenol |
| 4-n-Amyl | - Phenol |
| 4-tert-Amyl | - Phenol |
| 4-n-Hexyl | - Phenol |
| 4-n-Heptyl | - Phenol |

Mono- and Poly-Alkyl and Aromatic Halophenols

| | |
|---|---|
| Methyl | - p-Chlorophenol |
| Ethyl | - p-Chlorophenol |
| n-Propyl | - p-Chlorophenol |
| n-Butyl | - p-Chlorophenol |
| n-Amyl | - p-Chlorophenol |
| sec-Amyl | - p-Chlorophenol |
| n-Hexyl | - p-Chlorophenol |
| Cyclohexyl | - p-Chlorophenol |
| n-Heptyl | - p-Chlorophenol |
| n-Octyl | - p-Chlorophenol |

O-Chlorophenol

| | |
|---|---|
| Methyl | - o-Chlorophenol |
| Ethyl | - o-Chlorophenol |
| n-Propyl | - o-Chlorophenol |
| n-Butyl | - o-Chlorophenol |
| n-Amyl | - o-Chlorophenol |
| tert-Amyl | - o-Chlorophenol |
| n-Hexyl | - o-Chlorophenol |
| n-Heptyl | - o-Chlorophenol | p-Chlorophenol

| | |
|---|---|
| o-Benzyl | - p-Chlorophenol |
| o-Benzyl-m-methyl | - p-Chlorophenol |
| o-Benzyl-m, m-dimethyl | - p-Chlorophenol |
| o-Phenylethyl | - p-Chlorophenol |
| o-Phenylethyl-m-methyl | - p-Chlorophenol |
| 3-Methyl | - p-Chlorophenol |

-continued

| | |
|---|---|
| 3,5-Dimethyl | - p-Chlorophenol |
| 6-Ethyl-3-methyl | - p-Chlorophenol |
| 6-n-Propyl-3-methyl | - p-Chlorophenol |
| 6-iso-Propyl-3-methyl | - p-Chlorophenol |
| 2-Ethyl-3,5-dimethyl | - p-Chlorophenol |
| 6-sec Butyl-3-methyl | - p-Chlorophenol |
| 2-iso-Propyl-3,5-dimethyl | - p-Chlorophenol |
| 6-Diethylmethyl-3-methyl | - p-Chlorophenol |
| 6-iso-Propyl-2-ethyl-3-methyl | - p-Chlorophenol |
| 2-sec Amyl-3,5-dimethyl | - p-Chlorophenol |
| 2-Diethylmethyl-3.5-dimethyl | - p-Chlorophenol |
| 6-sec Octyl-3-methyl | - p-Chlorophenol |
| p-Bromophenol | |
| Methyl | - p-Bromophenol |
| Ethyl | - p-Bromophenol |
| n-Propyl | - p-Bromophenol |
| n-Butyl | - p-Bromophenol |
| n-Amyl | - p-Bromophenol |
| sec-Amyl | - p-Bromophenol |
| n-Hexyl | - p-Bromophenol |
| cyclohexyl | - p-Bromophenol |
| o-Bromophenol | |
| tert-Amyl | - o-Bromophenol |
| n-Hexyl | - o-Bromophenol |
| n-Propyl-m,m-Dimethyl | - o-Bromophenol |
| 2-Phenyl Phenol | |
| 4-chloro-2-methyl phenol | |
| 4-chloro-3-methyl phenol | |
| 4-chloro-3,5-dimethyl phenol | |
| 2,4-dichloro-3,5-dimethyl-phenol | |
| 3,4,5,6-terabromo-2-methyl-phenol | |
| 5-methyl-2-pentylphenol | |
| 4-isopropyl-3-methylphenol | |
| 5-chloro-2-hydroxydi-phenylemthane | |
| Resorcinol and its Derivatives | |
| Resorcinol | |
| Methyl | - Resorcinol |
| Ethyl | - Resorcinol |
| n-Propyl | - Resorcinol |
| n-Butyl | - Resorcinol |
| n-Amyl | - Resorcinol |
| n-Hexyl | - Resorcinol |
| n-Heptyl | - Resorcinol |
| n-Octyl | - Resorcinol |
| n-Nonyl | - Resorcinol |
| Phenyl | - Resorcinol |
| Benzyl | - Resorcinol |
| Phenylethyl | - Resorcinol |
| Phenylpropyl | - Resorcinol |
| p-Chlorobenzyl | - Resorcinol |
| 5-Chloro | -2,4-Dihydroxydiphenyl Methane |
| 4'-Chloro | -2,4-Dihydroxydiphenyl Methane |
| 5-Bromo | -2,4-Dihydroxydiphenyl Methane |
| 4'-Bromo | -2,4-Dihydroxydiphenyl Methane |
| Bisphenolic Compounds | |
| 2,2'-methylene bis (4-chlorophenol) | |
| 2,2'-methylene bis (3,4,6-trichlorophenol) | |
| 2,2'-methylene bis (4-chloro-6-bromophenol) | |
| bis (2-hydroxy-3,5-dichlorophenyl) sulfide | |
| bis (2-hydroxy-5-chlorobenzyl) sulfide | |
| Halogenated Carbanilides | |
| 3,4,4'-trichlorocarbanilide | |
| 3-trifluoromethyl-4,4'-dichlorocarbanilide | |
| 3,3',4-trichlorocarbanilide | |

The antibacterial agent is present in the oral composition in an effective antiplaque amount, typically about 0.01-5% by weight, preferably about 0.03-1%. The antibacterial agent is substantially water-insoluble, meaning that its solubility is less than about 1% by weight in water at 25° C. and may be even less than about 0.1%. If anionizable group is present solubility is determined at a pH at which ionization does not occur.

The preferred halogenated diphenyl ether is Triclosan. The preferred phenolic compound are hexyl resorcinol, 2,2'-methylene bis(4-chloro-6-bromophenol). The most preferred antibacterial antiplaque compound is Triclosan. Triclosan is disclosed in aformentioned U.S. Pat. No. 4,022,880 as an antibacterial agent in combination with an anticalculus agent which provides zinc ions. It is also disclosed as an antiplaque agent in a dentifrice formulated to contain a lamellar liquid crystal surfactant phase having a lamellar spacing of less than 6.0 mm and which may optionally contain a zinc salt in published European Patent application 0161898 of Lane et al and in a dentifrice containing zinc citrate trihydrate in published European Patent Application 0161899 to Saxton.

The linear molecularly dehydrated polyphosphate salts operative herein as anticalculus agents are well known, being generally employed in the form of their wholly or partially neutralized water soluble alkali metal (e.g. potassium and preferable sodium) or ammonium salts, and any mixtures thereof. Representative examples include sodium hexametaphosphate, sodium tripolyphosphate, disodium diacid, trisodium monoacid and tetrasodium pyrophosphates and the like. Linear polyphosphates correspond to $(NaPO_3)_n$ where n is about 2 to about 125. They are generally employed in the instant oral compositions in approximate weight amounts of 0.1 to 7%, more preferably 2 to 7%. When n is at least 3 in $(NaPO_3)_n$, said polyphosphates are glassy in character.

Particularly desirable anticalculus agents are tetraalkali metal pyrophosphates, including mixtures thereof, such as tetrasodium pyrophosphate, tetrapotassium pyrophosphate and mixtures thereof. An anticalculus agent comprising about 4.3% to about 7% by weight of the oral compositions wherein the weight ratio of tetrapotassium pyrophosphate to tetrasodium pyrophosphate is from about 4.3:2.7 to about 6:1 is especially preferred.

In order to optimize the anticalculus effectiveness of the oral composition, inhibitors against enzymatic hydrolysis of the polyphosphate are desirably present. Such agents are an amount of a fluoride ion source sufficient to supply 25 ppm. to 5,000 ppm. of fluoride ions, and 0% to 3% of a synthetic anionic polymeric polycarboxylate having a molecular weight of about 1,000 to about 1,000,000, preferably about 30,000 to about 500,000.

The sources of fluoride ions, or fluorine-providing component, as acid phosphatase and pyrophosphatase enzyme inhibitor component, are well known in the art as anti-caries agents. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium flourosilicate, ammonium florosilicate, sodium fluorozirconate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type or oral preparation, but it must be a non-toxic amount, generally abut 0.005 to about 3.0% in the preparation. In a dentifrice preparation, e.g. dental gel, toothpaste (including cream), toothpowder, or dental tablet, an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferable about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be present in an amount of about 0.1–3%, more typically about 0.76%.

In dentifrice preparations such as lozenges and chewing gum, the fluorine-providing compound is typically present in an amount sufficient to release up to about 500 ppm, preferably about 25 to 300 ppm by weight of fluoride ion. Generally about 0.005 to about 1.0 wt. % of such compound is present.

The synthetic anionic polymeric polycarboxylate is an inhibitor of alkaline phosphatase enzyme. Synthetic anionic polymeric polycarboxylates and their complexes with various cationic germicides, zinc and magnesium have been previously disclosed as anticalculus agents per se in, for example U.S. Pat. No. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al. However, only in aforementioned U.S. Pat. No. 4,627,977 to Gaffar et al is there disclosed use of such polycarboxylates alone for inhibiting salivary hydrolysis of pyrophosphate anticalculus agents, much less in combination with a compound providing a source of fluoride ion. It is to be understood that the synthetic anionic polymeric polycarboxylates so disclosed in these several patents are operative in the compositions and methods of this invention and such disclosures are to that extent incorporated herein by reference thereto.

The synthetic anionic polymeric polycarboxylates optionally but preferably employed herein are, as indicated above, well known, being often employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to about 1,000,000. These copolymers are available for example as Gantrez (AN 139 (M.W. 500,000), A.N. 119 (M.W. 250,000); and preferably S-97 Pharmaceutical Grade (M.W. 70,000), of GAF Corporation. The term "synthetic" is intended to exclude known thickening or gelling agents comprising carboxymethylcellulose and other derivatives of cellulose and natural gums.

Other operative polymeric polycarboxylates include those disclosed in U.S. Pat. No. No. 3,956,480 referred to above, such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. No. 4,138,477 and 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

Also useful herein are so-called carboxyvinyl polymers disclosed as toothpaste components in U.S. Pat. No. 3,980,767 to Chown et al; U.S. Pat. No. 3,935,306 to Roberts et al; U.S. Pat. No. 3,919,409 to Perla et al; U.S. Pat. No. 3,911,104 to Harrison, and U.S. Pat. No. 3,711,604 to Colodney et al. They are commercially available for example under the trademarks Carbopol 934, 940 and 941 of B. F. Goodrich, these products consisting essentially of a colloidally water-soluble polymer of polyacrylic acid crosslinked with from about 0.75% to about 2.0% of polyallyl sucrose or polyallyl pentaerythritol as cross linking agent.

The synthetic anionic polymeric polycarboxylate component is mainly a hydrocarbon with optional halogen and 0-containing substituents and linkages as present in for example ester, ether and OH groups, and when present is generally employed in the instant compositions in approximate weight amounts of 0.05 to 3%, preferably 0.05 to 2%, more typically employed in dentifrice compositions typically containing a dental abrasive and used in conjunction with brushing of the teeth, e.g. tooth pastes (including creams), gels, powders and tablets. Amounts in excess of these ranges may be employed for thickening or gelling purposes.

As indicated above, these polymeric polycarboxylates have been found to be effective inhibitors of alkaline phosphatase enzyme. Since this enzyme has little activity (for hydrolyzing pyrophosphate) at about pH 7.0 or below, the polymeric polycarboxylate component may, if desired, be omitted from oral preparations formulated to operate at such pH of 7.0 or below. Such omission however could reduce the versatility and anticalculus effectiveness of the present oral compositions over the. broad pH range of about 4.5 to about 10.

In oral preparations such as mouthwashes, lozenges and chewing gum, the fluorine-providing compound may be typically present in an amount sufficient to release up to about 500 ppm, preferably about 25 to about 300 ppm by weight of fluoride ion. Generally about 0.005 to about 1.0 wt. % of such compound is present.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or disodium hydrogen phosphate, sodium hydrogen phosphate, etc.).

In certain other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing material include the particulate thermosetting resins described in U.S. Pat. No. 3,070,510 of Dec. 15, 1962 such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50, 000 cm.$^2$/gm., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100 alkali metal almuino-silicate complexes are particularly useful, since they have refractive indices close to the refractive indices of gelling agent-liquid (including water and/or humectant)systems commonly used in dentifrices.

Many of the so-called "water-insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of material is larger than 37 microns.

The polishing material is generally present in the solid or pasty compositions in weight concentrations of about 10% to about 99%. Preferably, it is present in amounts ranging from about 10% to about 75% in toothpaste, and from about 70% to about 99% in toothpowder.

In a toothpaste, the liquid vehicle may comprise water and humectant typically in an amount ranging from about 10% to about 80% by weight of the preparation. Glycerine, propylene glycol, sorbitol, polypropylene glycol and/or polyethylene glycol (e.g. 400-600) exemplify suitable humectants/carriers. Also advantageous are liquid mixtures of water, glycerine and sorbitol. In clear gels where the refractive index is an important consideration, about 3-30 wt. % of water, 0 to about 70 wt. % of glycerine and about 20-80 wt. % of sorbitol are preferably employed.

Toothpastes, creams and gels typically contain a natural or synthetic thickener or gelling agent in proportions of about 0.1 to about 10, preferably about 0.5 to about 5wt. %. A suitable thickener is synthetic hectorite, a synthetic colloidal magnesium alkali metal silicate complex clay available for example as Laponite (e.g. CP, SP 2002,D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244).

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sobitan monosterate) and polypropyleneoxide (e.g. Pluronic materials).

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine and the like. Suitably, flavor and sweetening agents may together comprise from about 0.1% to 5% more of the preparation.

In the preferred practice of this invention an oral composition according to this invention such as a mouthwash or dentifrice containing the composition of the present invention is preferably applied regularly to dental enamel, such as every day or every second or third day or preferably from 1 to 3 times daily, at a pH of about 4.5 to about 9, generally about 5.5 to about 8, preferably about 6 to 8, for at least 2 weeks up to 8 weeks or more up to lifetime.

The compositions of this invention can be incorporated in lozenges, or in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The following examples are further illustrative of the nature of the present invention, but it is understood that the invention is not limited thereto. All amounts and proportions referred to herein and in the appended claims are by weight.

EXAMPLE 1

Slurries and solutions described below are prepared to determine effectiveness in terms of minimum inhibitory concentration (MIC) of various antibacterial agents against a variety of oral bacterial organisms implicated in formation of plaque and leading to gingivitis on dental surfaces. Soft plaque contains about $1.7 \times 10^{11}$ organism/gm. (net weight). The antibacterial agents are admixed with anionic materials, particularly anionic surface active agent often commonly employed in oral compositions and polyphosphate anticalculus agent.

Minimum inhibitory concentration (MIC) of antibacterial agent is used to evaluate the efficacy of the agent in vitro. MIC is defined as the minimum concentration in micrograms/ml of antibacterial agent at which the growth of bacteria is completely inhibited by the agent. The smaller the MIC value the greater is the efficacy of the antibacterial agent to inhibit the growth of the bacteria. The in vitro MIC data is related to the efficacy of the dentifrice in vivo since retention and release of antibacterial agent into the oral cavity after toothbrushing is in the range of mcg/ml.

In the Tables, following disclosure and following Examples, the agent Triclosan, 2,4,4'-trichloro-2'-hydroxydiphenyl ether is indicated as "TCHE"; the quaternary ammonium antibacterial agents benzthonium chloride is indicated as "BTC"; The biguanide chlorhexidine digluconate is indicated as "CH", sodium lauryl sulfate is indicated as "SLS"; the copolymer of maleic anhydride and methyl vinyl ether available from GAF corporation as "Gantrez S-97" is identified as "Gantrez"; tetrasodium pyrophosphate is identified as "pyrophosphate"; and sodium fluoride is identified as "NaF".

TABLE 1

| Test Solution | Minimum Inhibition Concentration (MIC) in mcg/ml | | | |
| --- | --- | --- | --- | --- |
| | Bacteriodes gingivalis | Bacteriodes intermedius | Actinobacillus actinomycetemcomitans | Streptococcus mutans |
| 1. 0.5% TCHE and 1% SLS in water | 2.5 | 2.5 | 5.0 | 25.0 |
| 2. 0.5% TCHE, 1% SLS, | 2.5 | 2.5 | 5.0 | 25.0 |

TABLE 1-continued

| Test Solution | Minimum Inhibition Concentration (MIC) in mcg/ml | | | |
|---|---|---|---|---|
| | Bacteriodes gingivalis | Bacteriodes intermedius | Actinobacillus actinomycetem-comitans | Streptococcus mutans |
| 1% Gantrez, 2% Pyrophosphate and 0.2% NaF in water | | | | |
| 3. 1% SLS in water | NE | NE | NE | NE |
| 4. 1% SLS, 1% Gantrez and 2% Pyrophosphate in water | NE | NE | NE | NE | note:
NE = not effective

The results indicate that TCHE in the presence of anionic surfactant inhibited four dental plaque organisms, *Bacteriodes gingivalis, Bacteroides intermedius, Actinobacillus actinomycetemcomitans* and *Strep. mutans* at 2.5 mcg/ml and 2.5 mcg/ml, 5.0 mcg/ml and 25.0 mcg/ml respectively(1). Similar antibacterial effect is seen in the presence of Gantrez/pyrophosphate/fluoride(2). SLS per se and a combination of SLS/Gantrez/pyrophosphate/fluoride was ineffective(3 and 4).

It is noteworthy that in human clinical tests with cationic antibacterial agents, 0.075% BTC dissolved in water is effective in reducing plaque formation while 0.075% BTC and 1% pyrosphosphate dissolved in water is not. Similarly, 0.1% CH dissolved in water is effective in reducing plaque formation while 0.1% CH and 1% sodium N-lauroyl sarcosinate dissolved in water is not.

EXAMPLE 2

The adsorption to and release from tooth minerals for antiplaque/ antitartar efficacy of agents is assessed by adsorption of antibacterial agent to saliva coated tooth mineral hydroxyapatite in the presence and the absence of pyrophosphate (soluble tetrasodium pyrophosphate)/Gantrez/NaF.

200 mg. of hydroxyapatite (HA) is treated with human saliva for 2 hours. The excess saliva is washed with a buffer and saliva coated HA is used for adsorption studies. Various concentrations of TCHE in SLS or in SLS/pyrophosphate/Gantrez/NaF are mixed with the coated HA and incubated at 37° for 3 hours under continuous agitation. At the end of incubation period, the mixtures are centrifuged, HA separated and the amounts of TCHE adsorbed determined by estimating TCHE in the supernatant at 283nM in a Gilford spectrophotometer. The amounts adsorbed are calculated by the difference between the amount added and the amount left in the supernatant after the incubation with coated HA. The table below summarizes the data.

TABLE 2

| Components and Concentrations | % of TCHE Adsorbed to Coated HA |
|---|---|
| 0.005% TCHE in 1% SLS | 80% |
| 0.01% TCHE in 1% SLS | 85% |
| 0.015% TCHE in 1% SLS | 85% |
| 0.02% TCHE in 1% SLS | 88% |
| 0.005% TCHE in 1% SLS; 0.5% Gantrez; 2% pyrophosphate/ 0.24% NaF | 80% |
| 0.01% TCHE in 1% SLS; 0.5% Gantrez; 2% pyrophosphate/ 0.24% NaF | 85% |
| 0.015% TCHE in 1% SLS; 0.5% Gantrez; 2% pyrophosphate/ 0.24% NaF | 86% |
| 0.02% TCHE in 1% SLS; 0.5% Gantrez; 2% pyrophosphate/ 0.24% NaF | 87% |

The data indicates that the addition of pyrophosphate/Gantrez/NaF does not impair adsorption of TCHE to saliva coated tooth minerals.

EXAMPLE 3

| Dentifrice Compositions | A Parts | B Parts | C Parts |
|---|---|---|---|
| Glycerine | 15.00 | 10.20 | 15.00 |
| Polyethylene Glycol 600 | 5.00 | 3.00 | 5.00 |
| Iota Carrageenan | 0.60 | — | 0.60 |
| Sodium Carboxymethyl Cellulose | — | 1.00 | — |
| Sodium Saccharin | 0.40 | — | 0.40 |
| Sodium Cyclamate | — | 3.00 | — |
| Sodium Fluoride | 0.243 | 0.243 | 0.243 |
| Deionized water | 15.08 | 29.907 | 23.657 |
| Titanium Dioxide | — | — | 0.50 |
| Sodium Benzoate | — | 0.50 | — |
| FD&C Blue No. 1 (1% Solution) | 0.400 | — | — |
| Sorbitol (70%) | 19.807 | 22.50 | 22.50 |
| Gantrez S-97 | 8.330* | 1.00** | 1.00** |
| Tetrasodium Pyrophosphate | 1.50 | 1.50 | 1.50 |
| Tetrapotassium Pyrophosphate | 4.50 | 4.50 | 4.50 |
| Precipitated Amorph. Hydrated Silica | 16.00 | 19.50 | — |
| Precipitated Amorp. Silica containing combined alumina | — | — | 16.00 |
| Silica Thickener | 7.00 | — | 5.50 |
| Flavor | 1.10 | 0.95 | 1.10 |
| Sodium Lauryl Sulfate | 1.20 | 1.20 | 1.20 |
| TCHE | 0.50 | 0.50 | 0.50 |

*liquid
**powder

EXAMPLE 4

The dentifrice described in Example 3A is compared with the same composition except without any TCHE and with added 0.50 parts of water. Aqueous extracts of each dentifrice are prepared as follows: 50 ml of distilled water is added to 1.0 gm of each dentifrice, mixed well for a couple of hours with stirring bar and centrifuged, after which the supernatant is collected as aqueous extract. Antibacterial activity of the dentifrice extracts are evaluated on *Bacteriodes gingivalis*. Results are summarized below.

TABLE 3

| Treatment | Inhibition of Growth of Bacteriodes Gingivalis % |
| --- | --- |
| Extract from dentifrice containing TCHE (1:500) | 100.0 |
| Extract from dentifrice without TCHE (1:500) | 0.0 |
| TCHE (5.0 mcg/ml) by itself | 100.0 |

These results indicate that TCHE antibacterial antiplaque agent is compatible in a dentifrice composition containing anionic surfactant plus pyrophosphate anticalculus ingredients with enzyme inhibitors Gantrez and NaF. Similar comparable effects prevail when each of hexyl resorcinol and 2,2'-methylene bis(4-chloro-6-bromophenol) replace TCHE.

EXAMPLE 5

| Mouthrinse | Parts |
| --- | --- |
| Tetrasodium Pyrophosphate | 2.00 |
| Gantrez S-97 | 0.25 |
| Glycerine | 10.00 |
| Sodium Fluoride | 0.05 |
| Pluronic F108 (Polyoxyethylene/Polyoxypropylene Block Copolymer) | 2.00 |
| TCHE | 0.10 |
| Flavor | 0.40 |
| Water | Q.S. to 100.00 |

EXAMPLE 6

Lozenge 75-80% Sugar
1-20% Corn Syrup
0.1-1.0 Flavor
2% Tetrasodium Pyrophosphate
0.25% Gantrez S-97
0.01 to 0.05% NaF
0.01 to 0.1% TCHE
1 to 5% Magnesium Stearate Lubricant
0.01 to 0.2% Water

EXAMPLE 7

| Chewing Gum | Parts |
| --- | --- |
| Gum base | 25.00 |
| Sorbitol (70%) | 17.00 |
| TCHE | 0.10 to 0.50 |
| Tetrasodium Pyrophosophate | 2.00 |
| Gantrez S.97 | 0.25 |
| NaF | 0.05 |
| Glycerine | 0.50 |
| Crystalline Sorbitol | 53.00 |
| Flavor and Water | Q.S. to 100.00 |

This invention has been described with respect to certain preferred embodiments and it will be understood that modifications and variations thereof obvious to those skilled in the art are to be included within the purview of this application and the scope of the appended claims.

We claim:

1. An oral composition comprising in an orally acceptable vehicle, an effective anticalculus amount of material comprising at least one wholly or partially neutralized alkali metal or ammonium tripolyphosphate or hexametaphosphate salt as anticalculus agent and an effective antiplaque amount of a substantially water insoluble noncationic antibacterial agent selected from the group consisting of halogenated diphenyl ethers, phenolic compounds and halogenated carbanilides.

2. The oral composition claimed in claim 1 wherein sodium tripolyphosphate is present as anticalculus agent.

3. The oral composition claimed in claim 1 wherein said at least one salt is present in amount of about 0.1-7% by weight and said substantially water insoluble nonocationic antibacterial agent is present in an amount of about 0.01-5% by weight.

4. The oral composition claimed in claim 3 wherein said antibacterial agent is a halogenated diphenyl ether.

5. The oral composition claimed in claim 4 wherein said halogenated diphenyl ether is 2,4,4'-trichloro-2-hydroxy-diphenyl ether.

6. The oral composition claimed in claim 3 wherein said antibacterial agent is a phenolic compound.

7. The oral composition claimed in claim 6 wherein said phenolic compound is resorcinol or a derivative thereof.

8. The oral composition claimed in claim 7 wherein said phenolic compound is hexyl resorcinol.

9. The oral composition claimed in claim 3 wherein there is present for the purpose of inhibiting hydrolysis of P—O—P bonds in said polyphosphate salts by phosphatase enzymes in saliva to orthophosphates which are relatively ineffective as inhibitors of hydroxyapatite formation, an amount of a fluoride ion source sufficient to supply 25 ppm. to 2,000 ppm. of fluoride ions and 0.05% to 3% of a water-soluble alkali metal or ammonium synthetic anionic linear polymeric polycarboxylate salt having a molecular weight of about 1,000 to about 1,000,000.

10. The oral composition claimed in claim 9 wherein said fluoride ion source is sodium fluoride and amount sufficient to supply 300 ppm. to 2,000 ppm. of fluoride ions and said polycarboxylate salt is about 0.1 to 2% of a water soluble alkali metal or ammonium salt of a copolymer of vinyl methyl ether and maleic acid or anhydride having a molecular weight of about 30,000 to about 500,000.

11. The oral composition claimed in claim 3 wherein sodium tripolyphosphate is present as anticalculus agent.

12. The oral composition claimed in claim 11 wherein said antibacterial agent comprises 2,4,4'-trichloro-2-hydroxydiphenyl ether.

13. The oral composition claimed in claim 3 wherein sodium hexametaphosphate is present as anticalculus agent.

14. The oral composition claimed in claim 13 wherein said antibacterial agent comprises 2,4,4'-trichloro-2-hydroxydiphenyl ether.

15. The oral composition claimed in claim 1 wherein said oral composition contains a dentally acceptable water-insoluble polishing agent and said oral compositions is a toothpowder, dental tablet, toothpaste or dentifrice.

16. The oral composition claimed in claim 15 wherein said oral composition contains about 10-80% by weight of a liquid phase comprising water and humectant, about 0.1-10% by weight a gelling agent and about 10-75% by weight of said polishing agent and said oral composition is a toothpaste or gel dentifrice.

17. The oral composition claimed in claim 16 wherein said polishing material is a silica polishing material.

18. The oral composition claimed in claim 15 wherein said oral composition contains about 70–99% by weight of said polishing material and said oral composition is a toothpowder.

19. The oral composition claimed in claim 1 wherein said oral composition contains about 90–99.9% by weight of a mixture of water and alcohol in a weight ratio of from about 1:1 to about 20:1 and said oral compositions is a mouthrinse.

20. The oral composition claimed in claim 19 wherein said alcohol is ethanol.

21. The oral composition claimed in claim 1 wherein said oral composition is a lozenge.

22. The oral composition claimed in claim 1 wherein said oral composition is a chewing gum.

23. The oral composition claimed in claim 1 wherein sodium hexametaphosphate is present as anticalculus agent.

24. The oral composition comprising about 10–75% by weight of a dentally acceptable water-insoluble polishing agent and an orally acceptable vehicle containing about 10–80% by weight of a liquid phase comprising water and humectant and about 0.1–10% by weight of a gelling agent, said oral composition being a dentifrice and there being present in said orally acceptable vehicle sodium tripolyphosphate anticalculus agent and an effective antiplaque amount of 2,4,4'-trichloro-2-hydroxydiphenyl ether antibacterial agent.

25. The oral composition claimed in claim 24 wherein said sodium tripolypohosphate is present in amount of at least about 0.1–7% by weight and said antibacterial agent is present in amount of about 0.01–5% by weight.

26. The oral composition claimed in claim 25 wherein there is present for the purpose of inhibiting hydrolysis of P—O—P bonds in said polyphosphate salts by phosphatase enzymes in saliva to polyphosphates which are relatively ineffective as inhibitors of hydroxyapatite formation, an amount of a fluoride ion source sufficient to supply 25 ppm. to 2,000 ppm. of fluoride ions and 0.05% to 3% of a water-soluble alakli metal or ammonium salt of a copolymer of vinyl methyl ether and maleic anhydride having a molecular weight of about 70,000.

* * * * *